United States Patent [19]

Le Fur et al.

[11] Patent Number: 5,391,770
[45] Date of Patent: Feb. 21, 1995

[54] PROCESS FOR PREPARING ASCORBIC ACID

[75] Inventors: Isidore Le Fur, Thiais; Jean-Paul Richard, Corbeil; Gérard Wolff, Thiais, all of France

[73] Assignee: Rhone Poulenc Rorer S.A., France

[21] Appl. No.: 171,988

[22] Filed: Dec. 23, 1993

Related U.S. Application Data

[63] Continuation of Ser. No. 40,589, Mar. 31, 1993, abandoned, which is a continuation of Ser. No. 796,878, Nov. 25, 1991, abandoned, which is a continuation of Ser. No. 536,461, Jun. 12, 1990, abandoned.

[30] Foreign Application Priority Data

Jun. 12, 1989 [FR] France ................. 89 07716

[51] Int. Cl.$^6$ ............................. C07D 307/62
[52] U.S. Cl. ................................. 549/315
[58] Field of Search .......................... 549/315

[56] References Cited

U.S. PATENT DOCUMENTS

| | | | |
|---|---|---|---|
| 2,265,121 | 12/1941 | Reichstein | 549/315 |
| 2,443,583 | 6/1948 | Mottern et al. | 549/315 |
| 4,491,668 | 1/1985 | Ikawa et al. | 549/315 |

FOREIGN PATENT DOCUMENTS

| | | |
|---|---|---|
| 779883 | 4/1935 | France . |
| 922949 | 6/1947 | France . |
| 63-17313 | 9/1963 | Japan . |

OTHER PUBLICATIONS

CA 51:2855b, 1957.
CA 60:9349d, 1964.
Chem. Abstr. vol. 90, No. 5, 29, Jan. 1979, No. 39204c.
Journal of Pharmaceutical Sciences, vol. 61, No. 8, Aug. 1972, pp. 1333, 1334.

*Primary Examiner*—C. Warren Ivy
*Assistant Examiner*—Ba K. Trinh
*Attorney, Agent, or Firm*—Morgan & Finnegan

[57] ABSTRACT

Process for preparing pure ascorbic acid from 2-keto-L-gulonic acid or its sodium salt, by carrying out the following successive steps:
  esterification of 2-keto-L-gulonic acid or its sodium salt
  lactonization to sodium ascorbate
  optional separation of the sodium ascorbate
  displacement of the ascorbic acid from its salt
  separation of the sodium sulphate
  separation and purification of the ascorbic acid from its methanolic or aqueous-methanolic solution.

6 Claims, No Drawings

PROCESS FOR PREPARING ASCORBIC ACID

This is a continuation of application Ser. No. 08/040,589, filed Mar. 31, 1993, now abandoned, which is a continuation of application Ser. No. 07/796,878, filed on Nov. 25, 1991, now abandoned, which is a continuation application of Ser. No. 07/536,461, filed on Jun. 12, 1990, now abandoned.

FIELD OF THE INVENTION

The present invention relates to the preparation of ascorbic acid from 2-keto-L-gulonic acid, optionally in salt form.

BACKGROUND OF THE INVENTION

It is known, e.g. from French Patent No. 922,949, to prepare ascorbic acid from esters of 2-keto-L-gulonic acid (2KLG-H), proceeding via an intermediate alkali metal salt of ascorbic acid. However, the implementation of this process does not permit ascorbic acid to be obtained with sufficient purity.

DETAILED DESCRIPTION OF THE INVENTION

It has now been found, and this forms the subject of the present invention, that practically pure, that is greater than 99.5%, ascorbic acid may be obtained after purification on acidic and basic resins of the ascorbic acid obtained by the action of a strong acid on sodium ascorbate, preferably isolated beforehand, which is itself obtained from 2-keto-L-gulonic acid or one of its alkali metal salts.

Practically pure ascorbic acid may be obtained by crystallization in water, in an alcohol such as methanol or in an aqueous-alcoholic medium such as an aqueous-methanolic solution.

According to the present invention, 2-keto-L-gulonic acid, optionally in salt form, is esterified by means of an alcohol in the presence of a strong acid, and the ester obtained is then converted, optionally in situ, by the action of a base in alcoholic solution, in the amount needed for quantitative consumption of the 2-keto-L-gulonic acid ester, to an alkali metal salt of ascorbic acid, which is isolated and then neutralized by the action of a strong acid, working in a solvent in which the alkali metal salt of the strong acid is insoluble and ascorbic acid is soluble. After separation of the alkali metal salt of the strong acid, the ascorbic acid is isolated from its solution.

The esterification of 2-keto-L-gulonic acid is carried out by means of an alcohol such as methanol or butanol, in the presence of a strong acid such as hydrochloric acid, sulfuric acid or sulfonic acids. The esterification is performed in the presence of an amount of strong acid which is preferably in the region of 2 mol % relative to the 2KLG-H employed, or by monitoring the apparent pH of the medium, which is maintained in the vicinity of 0.5 when hydrochloric acid or sulfuric acid is used.

Using an alkali metal salt of 2-keto-L-gulonic acid, preferably the sodium salt, it is necessary to use an amount of strong acid permitting the liberation of 2-keto-L-gulonic acid in situ and catalysis of the esterification reaction.

It can be advantageous to perform the esterification by means of butanol. In effect, butanol forms with water an azeotrope which can be distilled off during the esterification. In this way, it is hence possible to shift the equilibrium in the direction of esterification.

The use of butanol permits the esterification to be performed on a crude aqueous solution of 2-keto-L-gulonic acid, on fermentation broth from which biomass has been removed, for example by filtration, and which has been concentrated.

When an alkali metal salt of 2-keto-L-gulonic acid is employed, it can be advantageous to separate the alkali metal salt of the strong acid before carrying out the in situ conversion of the 2-keto-L-gulonic acid ester to the alkali metal salt of ascorbic acid. However, separation of the alkali metal salt of the strong acid is necessary when it is desired to isolate the 2-keto-L-gulonic acid ester after concentration of its alcoholic solution.

The esterification is generally performed at a temperature of between 50° and 70° C., and preferably in the region of 65° C.

The lactonization of the 2-keto-L-gulonic acid ester is generally performed by means of a base selected from inorganic bases (sodium hydroxide) and organic bases (sodium methylate) in alcoholic solution, which is added at a rate such that the base is immediately consumed and is supplied in the amount needed for quantitative consumption of the 2-keto-L-gulonic acid ester. It is especially advantageous to adjust the rate of flow of the alcoholic solution of the base in accordance with the pH value, and to stop the addition when the pH becomes close to 8.5.

The lactonization is generally performed at a temperature between 50° and 70° C., and preferably close to 65° C.

After lowering of the temperature in the vicinity of 30° C., the alkali metal salt of ascorbic acid (sodium ascorbate), which can contain up to 10% by weight of the alkali metal salt of 2-keto-L-gulonic acid (2KLG-Na), is separated by filtration.

The alkali metal salt of ascorbic acid (sodium ascorbate), containing, where appropriate, some of the alkali metal salt of 2-keto-L-gulonic acid (2KLG-Na), is neutralized by the action of a strong acid (sulfuric acid), working in methanolic or aqueous-methanolic solution which can contain up to 40% by weight of water, and preferably 15 to 25%, in which the alkali metal salt of the strong acid (sodium sulphate) is only sparingly soluble.

It is especially advantageous to add the pure or dilute strong acid at a constant rate adjusted in accordance with the pH so as to neutralize the alkali metal salt of ascorbic acid and, at least partially, the alkali metal salt of 2-keto-L-gulonic acid. The pH at the end of the acidification is generally between 1.5 and 3.5, and preferably in the region of 3.

The alkali metal salt of the strong acid and, where appropriate, the unneutralized alkali metal salt of 2-keto-L-gulonic acid are separated by filtration. The 2-keto-L-gulonic acid may be recovered by washing the filter cake with a strong acid (sulfuric acid) in methanolic solution and may thus be recycled into the esterification phase.

The neutralization of the alkali metal salt of ascorbic acid may also be carried out by passing an aqueous solution of the alkali metal salt of ascorbic acid through a column of sulfonic acid resin.

From the methanolic or aqueous-methanolic solution, obtained after separation of the alkali metal salt of the strong acid and the unhydrolyzed alkali metal salt of 2-keto-L-gulonic acid, pure ascorbic acid can be isolated according to one of the following methods:

1) The solution may be filtered on a column of sulfonic acid resin and then on a column of basic resin (tertiary amine type) in order to remove the residual alkali metal salt of the strong acid, and then decolorized by treatment by means of decolorizing charcoal. The purified solution is then concentrated under reduced pressure in order to crystallize the pure ascorbic acid, which is separated by filtration.

The filtrates, after suitable treatment, may be recycled to the esterification or acidification step.

2) The solution may be concentrated under reduced pressure in order to crystallize the crude ascorbic acid, which is separated by filtration. The crude ascorbic acid is then dissolved in water or methanol, and the solution obtained is purified by passage through a sulfonic acid resin and then through a basic resin in order to remove the residual alkali metal salt of the strong acid, and finally decolorized by treatment by means of decolorizing charcoal. The solution thus purified is concentrated under reduced pressure in order to bring about crystallization of the pure ascorbic acid, which is separated by filtration.

The crystallization filtrates of crude ascorbic acid or of pure ascorbic acid can, after suitable treatment and according to their composition, be recycled to the esterification, lactonization or acidification step.

From the aqueous solution obtained after neutralization of an aqueous solution of an alkali metal salt of ascorbic acid by passage through a sulfonic acid resin, pure ascorbic acid may be obtained after decolorization of the solution by treatment by means of decolorizing charcoal, concentration under reduced pressure and filtration of the pure ascorbic acid which crystallizes.

EXAMPLES

The examples which follow, given without implied limitation, show how the invention may be put into practice.

EXAMPLE 1

Methanol (1925 g or 2436 cc; 60.1 moles) and pure 2KLG-H.2H$_2$O (450 g; 2.12 moles) are introduced into a 3-liter reactor. The mixture is stirred at 65° C. until dissolution is complete. 97% strength sulfuric acid (4.4 g or 2.39 cc; 0.043 mole) is then added and stirring is thereafter continued for 4 hours 30 minutes at 65° C.

The assayed yield of 2-keto-L-gulonic acid methyl ester is 96%.

The solution obtained (2379 g), which contains 2-keto-L-gulonic acid methyl ester (17.7% by weight or 423.3 g; 2.03 moles) and 2-keto-L-gulonic acid (0.007% or 16.5 g; 0.085 mole), is introduced into a 3-liter reactor and maintained at 65° C. A 3.7N methanolic sodium hydroxide solution (548 g or 590 cc; 2.2 moles of sodium hydroxide) is added at 65° C. in the course of 2 hours 30 minutes, the following rates of flow being observed:
98.8% of the volume of sodium hydroxide is introduced at the rate of 230 cc/hour when the pH is below 8.5,
1.2% of the volume of sodium hydroxide is introduced at the rate of 80 cc/hour when the pH is above 8.5.

The addition of sodium hydroxide is stopped when the pH becomes higher than 8.7.

After cooling to 30° C., the slurry obtained is filtered. The filter cake is washed with methanol (3×225 cc) at a temperature in the region of 20° C.

After drying, a product (404.1 g) is obtained containing:
sodium ascorbate (92% by weight or 371.7 g; 1.88 mole)
2-keto-L-gulonic acid sodium salt (8.7% by weight or 35.2 g; 0.16 mole).

EXAMPLE 2

Methanol (1270 g or 1607 cc; 39.7 moles), water (317.5 g; 17.6 moles) and sodium ascorbate (388.2 g) assaying at 91.9% by weight of sodium ascorbate (or 356.7 g) and 8.5% by weight of 2-keto-L-gulonic acid sodium salt (or 33 g), obtained under the conditions of Example 1, are introduced into a 3-liter reactor.

The reaction mixture is stirred at a temperature in the region of 20° C. and is then acidified with 97% strength sulfuric acid (98.7 g; 56.6 cc; 0.977 mole), which is added in the course of 1 hour on the basis of 98% of the volume of sulfuric acid at the rate of 60 cc/hour (pH above 3.6) and 2% of the volume of sulfuric acid at the rate of 6 cc/hour (pH below 3.6). The addition of sulfuric acid is stopped when the pH is below 3.

During the addition of sulfuric acid, the temperature of the reaction mixture should be maintained at 40° C.

The sodium sulphate which has precipitated is separated by filtration at 40° C. and washed with methanol (474 g).

The filtrate and washings are combined. An aqueous-methanolic solution (2273 g) is obtained containing:
ascorbic acid (13.85% by weight or 314.9 g; 1.79 mole)
2-keto-L-gulonic acid (0.95% by weight or 21.62 g; 0.11 mole)
sodium sulphate (0.16% by weight or 3.6 g; 0.025 mole).

EXAMPLE 3

Under the conditions of Example 2, an aqueous-methanolic solution of ascorbic acid (2042 g) containing 14.97% by weight of ascorbic acid (or 305.7 g; 1.74 mole) and 0.8% by weight of 2-keto-L-gulonic acid (or 16.33 g; 0.084 mole) is prepared. The solution is concentrated under reduced pressure at 48° C. in a continuously fed crystallizer initially containing a sediment saturated with ascorbic acid in the presence of 4 g of seed crystals.

When concentration is complete, the slurry is filtered at 30° C. The filter cake is washed with methanol (220 cc; 174 g) and then dried under reduced pressure at a temperature in the region of 20° C. A product (249.1 g) containing ascorbic acid (99% by weight) is thereby obtained.

EXAMPLE 4

Methanol (861 g or 1090 cc; 26.9 moles) and crude ascorbic acid (130 g) assaying at 98.4% by weight of ascorbic acid (or 127.9 g; 0.72 mole) are introduced into a 2.5-liter reactor.

The reaction mixture is stirred and is heated to 50° C. until the ascorbic acid has dissolved.

The solution is passed at 50° C. in the course of 45 minutes through sulfonic acid resin (Amberlite IRN 77) (50 cc). The resin is washed with methanol (50 cc). The solution and washings are combined. The solution obtained is passed at 50° C. in the course of 45 minutes through basic resin (Amberlite A368) (8 g). The resin is washed with methanol (50 cc). The solution and washings are combined and then treated with decolorizing charcoal (Acticarbon L3S treated beforehand with sulfuric acid for 15 minutes at 50° C.) (1.3 g).

The solution is filtered and the charcoal is washed with methanol (50 cc). The filtrate and washings are combined. A solution (1094.4 g) containing ascorbic acid (10.89% by weight or 119.18 g; 0.68 mole) is thereby obtained.

The solution thereby obtained is concentrated by distillation of the methanol at 65° C. After a portion (150 cc) of methanol has been distilled off, pure ascorbic acid (2 g) is added in order to initiate crystallization, and concentration is then resumed. When crystallization is complete, the mixture is cooled to 30° C. and the slurry obtained is then filtered. The filter cake is dried under reduced pressure at a temperature in the region of 20° C. Pure ascorbic acid (85.6 g) is thereby obtained.

EXAMPLE 5

Methanol (665 g or 842 cc; 20.8 moles) and crude 2-keto-L-gulonic acid (153.7 g) assaying at 78.6% are introduced into a 3-liter reactor.

The reaction mixture is heated to 65° C. with stirring until dissolution is complete.

97% strength sulfuric acid (1.2 g; 0.65 cc; 0.12 mole) is then added and the mixture is thereafter stirred for 6 hours at 65° C.

The solution obtained (842.6 g), which contains 2-keto-L-gulonic acid methyl ester (14% by weight or 118 g; 0.56 mole), 2-keto-L-gulonic acid (1.5% by weight or 77 g; 0.067 mole) and ascorbic acid (0.7% by weight or 6 g; 0.034 mole), is concentrated at 40° C. under reduced pressure (3 mm Hg; 39.9 kPa) for 2 hours. After cooling, the product which precipitates is separated by filtration. A product (78.4 g) containing 2-keto-L-gulonic acid methyl ester (98.3% by weight or 77 g; 0.37 mole) and 2-keto-L-gulonic acid (1.7% or 6 g; 0.007 mole) is thereby obtained.

The filtrate (398 g), which contains 2-keto-L-gulonic acid methyl ester (16% by weight or 63 g; 0.30 mole), 2-keto-L-gulonic acid (4.4% by weight or 17.5 g; 0.09 mole) and ascorbic acid (1.6% by weight or 6.5 g; 0.037 mole), is concentrated at 40° C. under reduced pressure (300 mm Hg; 39.9 kPa) for 2 hours. After cooling, the product which precipitates is separated by filtration. After drying, a product (27 g) is obtained containing 2-keto-L-gulonic acid methyl ester (96.3% by weight or 26 g; 0.125 mole) and 2-keto-L-gulonic acid (3.5% by weight or 0.95 g; 0.005 mole).

EXAMPLE 6

Methanol (197.5 g or 250 cc; 6.17 moles) and 2-keto-L-gulonic acid methyl ester (52 g; 0.25 mole) are introduced into a 2-liter reactor. The stirred reaction mixture is heated to 65° C. Sodium bicarbonate (21 g; 0.25 mole) is then added. The evolution of carbon dioxide ceases after 2 hours 40 minutes. Stirring at 65° C. is maintained for a total period of 4 hours 15 minutes. After cooling to a temperature in the region of 20° C., the reactor is emptied and rinsed with methanol (347.4 g). The slurry is concentrated to dryness under reduced pressure. A product (51.5 g) containing sodium ascorbate (65.3% by weight or 33.63 g; 0.19 mole) is thereby obtained.

EXAMPLE 7 n-Butanol (218.7 g or 270 cc; 2.95 moles) and crude 2-keto-L-gulonic acid (50 g) assaying at 83.5% are introduced into a 500-cc reactor. p-Toluene-sulfonic acid (2.25 g; 0.013 mole) is added.

The reaction mixture is stirred. The butanol is evaporated off under reduced pressure (110 mm Hg; 14.6 kPa) at 70° C. The level is kept constant in the reactor by adding pure butanol. The mixture becomes homogeneous after 3 hours 30 minutes of heating. The esterification yield is 90%.

The 2-keto-L-gulonic acid butyl ester is crystallized from the butanol solution by cooling. After filtration, the 2-keto-L-gulonic acid butyl ester is washed and then dried.

EXAMPLE 8 n-Butanol (183 g or 226 cc; 2.47 moles) and 97% pure 2-keto-L-gulonic acid butyl ester (39.8 g; 0.154 mole) are introduced into a jacketed dropping funnel and the solution is maintained at 70° C.

n-Butanol (48 g or 59 cc) and pure sodium hydroxide (6.16 g; 0.154 mole) are introduced into a second jacketed dropping funnel.

n-Butanol (13.8 g or 17 cc; 0.18 mole), pure ascorbic acid (1.66 g; 0.009 mole) and sodium methylate (0.51 g; 0.009 mole) are introduced into the reactor.

The contents of the two dropping funnels are added simultaneously in the course of 2 hours while the reactor temperature is maintained at 62° C.

Sodium ascorbate precipitates during the reaction.

After cooling to a temperature in the region of 20° C., the sodium ascorbate is separated by filtration and washed with n-butanol (97 g or 120 cc) and n-hexane (198 g or 300 cc).

A product (31.8 g) containing sodium ascorbate (85.5% or 0.137 mole) is thereby obtained.

EXAMPLE 9

Methanol (395 g or 500 cc), pure 2-keto-L-gulonic acid monohydrate (100 g; 0.471 mole) and 12N hydrochloric acid (2 cc or 2.4 g) are introduced into a 2-liter reactor. The mixture is heated with stirring for 2 hours at 65° C. It is neutralized by adding 10N sodium hydroxide (2.5 cc).

After concentration to dryness under reduced pressure, a product (100.3 g) containing 2-keto-L-gulonic acid methyl ester (86.7%; 0.417 mole) is obtained.

EXAMPLE 10

Methanol (158 g or 200 cc; 4.9 moles), 97% strength sulfuric acid (12.41 g or 6.74 cc; 0.123 mole) and 2-keto-L-gulonic acid sodium salt (44.35 g) assaying at 83.3% (0.171 mole) are introduced into a 500-cc reactor.

The stirred mixture is heated to 65° C. for 4 hours 30 minutes. 3.5N methanolic sodium hydroxide (11.5 cc) is added so as to bring the pH to 4.

The sodium sulphate which has precipitated is separated by filtration and washed with methanol (100 g or 126 cc).

The filtrate and washings are combined. A solution containing 2-keto-L-gulonic acid methyl ester (32.7 g) is thereby obtained.

EXAMPLE 11

Methanol (130 g or 164 cc; 4.06 moles), 2-keto-L-gulonic acid (30.0 g) assaying at 92.3% (0.142 mole) and sulfonic acid resin (Amberlite IRN 77) (80 cc) are introduced into a 500-cc reactor.

The reactor is purged with nitrogen and then heated to 65° C. with stirring for 4 hours 30 minutes.

The yield is 95%.

EXAMPLE 12

Methanol (99 g or 125 cc; 3 moles) and sodium ascorbate (23.5 g) containing 93.5% of sodium ascorbate (or 22 g; 0.11 mole) and 3.4% of 2-keto-L-gulonic acid sodium salt (or 0.8 g; 0.0037 mole) are introduced into a 500-cc reactor.

The stirred mixture is heated to 55° C. and a 5M solution of sulfuric acid in methanol is then added in the course of 1 hour 15 minutes. The slurry obtained is maintained at 55° C. for 15 minutes. The sodium sulphate which has precipitated is separated by filtration and then washed with methanol (2×25 cc or 39 g).

The filtrate and washings are combined. A methanolic solution (160 g) containing ascorbic acid (11.2% by weight or 17.92 g; 0.101 mole) and 2-keto-L-gulonic acid (0.19% by weight or 0.304 g; 0.0015 mole) is thereby obtained.

EXAMPLE 13

A methanolic solution (2973.3 g) containing ascorbic acid (10.1% by weight or 300.3 g; 1.7 mole) and 2-keto-L-gulonic acid methyl ester (0.72 % by weight or 21.4 g; 0.10 mole) is introduced into a 3-liter reactor.

The solution is concentrated at 40° C. under reduced pressure (300 mm Hg; 39.9 kPa). When the ascorbic acid concentration of the solution reaches 13.5% by weight, crystallization is initiated by adding ascorbic acid (2 g). Concentration is continued under the same conditions. The precipitate is separated by filtration and washed with methanol (198 g or 250 cc) at a temperature in the region of 20° C. After drying under reduced pressure at a temperature in the region of 20° C., ascorbic acid (238.5 g) assaying at 97.3% is obtained.

EXAMPLE 14

Methanol (213 g or 270 cc; 6.66 moles) and sodium ascorbate (53.8 g) containing 91% of sodium ascorbate (or 49.2 g; 0.25 mole) and 2-keto-L-gulonic acid sodium salt (4.6 g; 0.0213 mole) are introduced into a 1-liter reactor.

The stirred mixture is heated to 55° C. and a 5M solution of sulfuric acid in methanol is then added slowly in the course of 1 hour to pH 2.

Sodium sulphate precipitates. Stirring is maintained at 55° C. for 15 minutes. The sodium sulphate is separated by filtration and then washed with methanol (2×20 cc or 31 g).

The filtrate and washings are combined. A methanolic solution (263.5 g) containing ascorbic acid (15.95% by weight or 42 g; 0.24 mole) and 2-keto-L-gulonic acid (1.44% by weight or 3.8 g; 0.02 mole) is thereby obtained.

EXAMPLE 15

Methanol (2375 g or 3 liters; 74.2 moles) and sodium ascorbate (391 g) containing 93.09% of sodium ascorbate (or 364 g; 1.84 mole) and 2-keto-L-gulonic acid sodium salt (25.4 g; 0.12 mole) are introduced into a 3-liter reactor. The mixture is stirred at a temperature in the region of 20° C.

97% strength concentrated sulfuric acid (109.1 g or 59.2 cc) is added in the course of 1 hour 10 minutes, the following rates of flow being observed:

98% of the volume of sulfuric acid is introduced at the rate of 60 cc/hour when the pH is above 3.6, 2% of the volume of sulfuric acid is introduced at the rate of 5 cc/hour when the pH is below 3.6.

The addition of sulfuric acid is stopped when the pH becomes lower than 1.5. During the acidification, the temperature of the reaction mixture is kept below or equal to 40° C.

The sodium sulphate precipitates.

After the stirring is stopped, the supernatant methanol layer is partially drawn off and filtered. The sodium sulphate separated by filtration is resuspended in the remaining slurry, which is filtered at 40° C.

The sodium sulphate cake is washed with methanol (3×167 cc). The washings are combined with the methanol filtrate. A methanolic solution (2917.2 g) containing ascorbic acid (10.47% by weight or 305.4 g; 1.73 mole), 2-keto-L-gulonic acid (0.17% by weight or 4.95 g; 0.025 mole) and 2-keto-L-gulonic acid methyl ester (0.69% by weight) is thereby obtained.

EXAMPLE 16

Outgassed water (118 cc; 6.55 moles) and sodium ascorbate (30 g) assaying at 95.8% by weight (or 0.145 mole) are introduced into a 500-cc reactor.

The mixture is stirred at a temperature in the region of 20° C. until dissolution is complete. The solution is passed in the course of 55 minutes at 22° C. through sulfonic acid resin (Amberlite IRN 77) (130 cc), washed beforehand.

The resin is washed with outgassed water (225 cc). The washings are combined with the demineralized solution. The solution is treated with decolorizing charcoal (2 g) for 1 minute at 60° C. After separation of the charcoal by filtration, the latter is washed with water (100 cc).

The filtrate and washings are combined. The solution is concentrated under reduced pressure (60 mm Hg; 8 kPa) at 40° C. The product which crystallizes is separated by filtration, washed with methanol (63.2 g; 80 cc) and then dried.

Pure ascorbic acid (17.8 g) is thereby obtained.

EXAMPLE 17

Demineralized water (225 g; 12.5 moles) and crude ascorbic acid (78 g) assaying at 97.95% by weight are introduced into a 1-liter reactor. The stirred reaction mixture is heated to 50° C. until dissolution is complete and then treated with decolorizing charcoal (Acticarbon L3S washed beforehand with sulfuric acid) (1.6 g) for 15 minutes at 50° C. The decolorizing charcoal is separated by filtration and washed with demineralized water (40 cc).

Sulfonic acid resin (Amberlite IRN 77) (32 cc) is added to the combined filtrate and washings.

The reaction mixture is stirred for 2 hours at 50° C. It is filtered and the resin is washed with demineralized water (40 cc). The filtrate and washings are combined.

Basic resin (Amberlite A368) (16.5 cc) is added to the solution obtained. The mixture is stirred for 45 minutes at 45° C. The resin is separated by filtration and washed with demineralized water (40 cc).

The filtrate and washings are combined. An aqueous solution (388 g) containing ascorbic acid (18.2% by weight or 70.6 g; 0.40 mole) is thereby obtained.

The solution thereby obtained (382.4 g) is concentrated under reduced pressure (40 mm Hg; 5.3 kPa).

When crystallization is complete, the insoluble matter is separated by filtration after cooling to 35° C. The cake is washed with ice-cold water (20 cc) and ice-cold ethanol (40 cc; 32 g). The filtrate and washings are combined. A solution (65.7 g) containing ascorbic acid (13.11% by weight or 8.61 g; 0.049 mole) is thereby obtained.

The ascorbic acid cake is dried under reduced pressure at a temperature in the region of 20° C. Pure ascorbic acid (59.6 g) is thereby obtained.

EXAMPLE 18

A solution (2032.8 g) containing methanol (1358.5 g; 42.4 moles), water (336.5 g; 18.7 moles), ascorbic acid (312.6 g; 1.77 mole), 2-keto-L-gulonic acid (6.5 g; 0.033 mole) and 2-keto-L-gulonic acid methyl ester (18.7 g; 0.09 mole) is introduced into a 3-liter reactor.

The solution is passed through columns of resins mounted in series, the first containing sulfonic resin (Amberlite IRN 77) (220 cc) and the second containing basic resin (Amberlite A368) (110 cc), at 40° C. at the rate of flow of 3 liters/hour.

The resins are washed with methanol (316 g).

The filtrate and washings are combined. A slurry of decolorizing charcoal, consisting of methanol (118 g; 149 cc) and decolorizing charcoal (Acticarbon L3S treated beforehand with sulfuric acid) (5 g) is added.

The solution is stirred for 15 minutes at 40° C. The charcoal is separated by filtration and washed with methanol (316 g; 400 cc).

The filtrate and washings are combined. A solution (2717 g) containing methanol (1994 g), water (423 g), ascorbic acid (274.7 g; 1.56 moles), 2-keto-L-gulonic acid (8.4 g; 0.043 mole) and 2-keto-L-gulonic acid methyl ester (16.8 g) is thereby obtained.

A solution (1752.9 g) obtained under the conditions described above, containing methanol (1159 g), water (290 g), ascorbic acid (303.8 g; 1.72 mole) and 2-keto-L-gulonic acid (20.86 g; 0.107 mole) is introduced into a 3-liter reactor.

A suspension consisting of methanol (19 g), water (43 g) and pure ascorbic acid (35 g; 0.2 mole) is prepared in a crystallizer.

The reaction mixture is stirred under reduced pressure (85 mm Hg; 11.4 kPa) at 40° C., and the aqueous-methanolic solution is then added so as to maintain the temperature at 40° C.

When crystallization is complete, the slurry is filtered at 40° C. The filter cake is washed with methanol (210 g; 266 cc) at 40° C.

After drying under reduced pressure at a temperature in the region of 20° C., pure ascorbic acid (170.0 g) is obtained.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A process for the preparation of pure ascorbic acid from an alkali metal ascorbate comprising:
    a) displacing ascorbic acid from a methanol or an aqueous-methanolic solution of alkali metal ascorbate and forming a methanolic or aqueous methanolic solution of ascorbic acid;
    wherein the ascorbic acid is displaced from alkali metal ascorbate by adding a sufficient quantity of a strong acid to the ascorbate/methanol or ascorbate/aqueous methanolic solution to maintain the pH between about 1.5 and about 3.5, and wherein the alkali metal salt of the strong acid formed is only sparingly soluble in the methanol or aqueous-methanolic solution; and further comprising
    b) separating the alkali metal salt of the strong acid from the displacement mixture formed in step a);
    c) obtaining a methanolic or aqueous-methanolic solution of ascorbic acid;
    d) passing the solution of step c) through a sulfonic resin and then a tertiary amine resin in order to remove the residual alkali metal salt of the strong acid, without absorption of the ascorbic acid; and
    e) isolating the pure ascorbic acid from the methanolic or aqueous-methanolic solution of step d).

2. A process according to claim 1, wherein the alkali metal is sodium.

3. A process according to claim 1, wherein the sodium ascorbate is obtained by
    i) esterifying 2-keto-L-gulonic acid, optionally in the form of a sodium salt, in the presence of a strong acid selected from the group consisting of sulfuric, hydrochloric and sulfonic acids,
    ii) converting the 2-keto-L-gulonic acid ester, optionally in situ, to sodium ascorbate by means of an inorganic or organic base in alcoholic solution, and
    iii) optionally separating the sodium ascorbate which precipitates.

4. A process according to claim 1, further comprising,
    f) concentrating the methanolic or aqueous-methanolic solution of step c),
    g) separating the ascorbic acid from the concentrated solution of step f) and dissolving the separated ascorbic acid in water,
    h) passing the aqueous solution of step ii) through acidic resin and then a tertiary amine resin and
    i) crystallizing the pure ascorbic acid from its decolorized aqueous solution and separating by filtration.

5. A process according to claim 1, further comprising
    f) concentrating the methanolic or aqueous-methanolic solution of step c),
    g) separating the ascorbic acid from the concentrated solution of step f) and dissolving the separated ascorbic acid in methanol,
    h) passing the methanolic solution of step g) through acidic and tertiary amine resins and
    i) crystallizing the pure ascorbic acid from its decolorized methanolic solution and separating by filtration.

6. A process according to claim 1, wherein the ascorbic acid is isolated by crystallizing the pure ascorbic acid from its decolorized methanolic solution or aqueous-methanolic solution and separating by filtration.

* * * * *